United States Patent [19]

Schollmeier et al.

[11] Patent Number: 5,157,106

[45] Date of Patent: Oct. 20, 1992

[54] N-TERMINAL DELETIONS OF LYMPHOTOXIN, THEIR PREPARATION AND USE

[75] Inventors: Klaus Schollmeier, Hemsbach; Achim Moeller, Limburgerhof; Wolfgang Koerwer, Ludwigshafen; Thomas Doerper, Bissersheim; Heinz Hillen, Ludwigshafen; Lothar Daum, Otterstadt; Franz Emling, Ludwigshafen; Gerhard Keilhauer, Dannstadt-Schauernheim, all of Fed. Rep. of Germany

[73] Assignee: BASF Aktiengesellschaft, Ludwigshafen, Fed. Rep. of Germany

[21] Appl. No.: 61,439

[22] Filed: Jun. 15, 1987

[30] Foreign Application Priority Data

Jun. 20, 1986 [DE] Fed. Rep. of Germany ....... 3620656

[51] Int. Cl.$^5$ .................. C07K 13/00; A01K 37/02
[52] U.S. Cl. .................. 530/351; 530/395; 530/820; 930/143; 930/144; 424/85.1; 435/69.5
[58] Field of Search .................. 530/350, 351, 395; 435/68, 70; 424/85.1

[56] References Cited

U.S. PATENT DOCUMENTS

| | | | |
|---|---|---|---|
| 4,568,640 | 2/1986 | Rubin | 435/68 |
| 4,677,063 | 6/1987 | Mark et al. | 530/351 |
| 4,677,064 | 6/1987 | Mark et al. | 530/351 |
| 4,752,575 | 6/1988 | Granger et al. | 530/351 |
| 4,782,139 | 11/1988 | DiMarchi | 530/407 |

FOREIGN PATENT DOCUMENTS

| | | |
|---|---|---|
| 0164965 | 12/1985 | European Pat. Off. . |
| 0232107 | 8/1987 | European Pat. Off. . |
| 8304262 | 12/1982 | PCT Int'l Appl. .................. 435/68 |

OTHER PUBLICATIONS

Pennica et al., Nature 312, 1984, pp. 724–729.
Kakutani et al, CA vol. 108, 1988, #92969x.
Iwasa et al, CA vol. 109, 1988, #123811s.
The Journal of Biological Chemistry, vol. 260, No. 4, Feb. 25, 1985, pp. 2334–2344, "Primary Structure of Human Lymphotoxin Derived from 1788 Lymphoblastoid Cell Line", Aggarwal et al.
Rubin et al, PNAS, 82, 1985, p. 6637.
Bachmair et al, Science 234, 1986, pp. 179–186.
Wells et al, Gene 34 (1985) pp. 315–323.
Ruddle and Waksman, J. Exp. Med. 128, 1267–1279; 1968.
Granger and Kolb, J. Immun. 101, 111–120; 1968.
Rosenau, W. Fed. Proc. 27, 34–38; 1968.
Sawada and Osawa, Jap. J. Exp. Med. 46, 263–267; 1976.
Granger et al., J. Cell. Immun. 38, 388–402; 1978.
Rundell and Evans, Immun. 3, 9–18; 1981.
Granger et al. J. Lymphokine Res. 1, 45–49; 1982.
Ruddle et al. J. Lymphokine Res. 2, 23–31, 1983.
Khan et al, Proc. Soc. Exp. Biol. Med. 169, 291–294; 1982.
Papermaster et al. Cancer 45, 1248–1253; 1980.
Ranson et al., J. Natn. Cancer Inst. 69, 741–744; 1982.
Gray et al. Nature 312, 721–724; 1984.
Ruff and Giffort, Lymphokines vol. 2, Pick, E. ed. 235–275 Academic Press New York 1981.
Carswell et al. Proc. Natl. Acad. Sci. 72, 3666–3670; 1975.
Evans, Canc. Immunol. Immunother. 12, 181–190; 1982.
Ruff and Giffort, Infect. Immun. 31, 380–385; 1981.
Williamson et al, Proc. Natl. Acad. Sci. 80, 5397–5401; 1983.
Williams and Bellanti, J. Immunol. 130, 518–520; 1983.
Stone-Wolff et al. J. Exp. Med. 159, 828–843; 1984.
Lee et al, J. Immunol. 133, 1083–1086; 1984.
Powell et al, Lymphokine Res. 4, 13–26; 1985.
Nedwin et al. Nucl. Acid Res. 13, 6361–6373; 1985.
Aggarwal et al. J. Biol. Chem. 259, 686–691; 1984.
Maniatis et al., Molecular Cloning, Cold Spring Harbor Laboratory, 1982.
Beck and Bolmer, Nucl. Acid. Res. 8, 3011–3027; 1980.

Primary Examiner—Garnette D. Draper
Attorney, Agent, or Firm—Oblon, Spivak, McClelland, Maier & Neustadt

[57] ABSTRACT

Polypeptides which differ from lymphotoxin by the absence of amino acids at the N-terminal end of the lymphotoxin are described. The polypeptides can be prepared by gene manipulation and are suitable, alone or in combination with lymphokines, as pharmaceuticals.

3 Claims, 8 Drawing Sheets

FIG. 1

```
-34
Met Thr Pro Pro Glu Arg Leu Phe Leu Pro Arg Val Cys Gly Thr Thr Leu His
                                                      -1  +1
Leu Leu Leu Gly Leu Leu Val Leu Leu Pro Gly Ala Gln Gly Leu Pro
Gly Val Gly Leu Thr Pro Ser Ala Ala Gln Thr Ala Arg Gln His Pro Lys Met
         +24 +25 +26
His Leu Ala His Ser Thr Leu Lys Pro Ala Ala His Leu Ile Gly Asp Pro Ser
Lys Gln Asn Ser Leu Leu Trp Arg Ala Asn Thr Asp Arg Ala Phe Leu Gln Asp
Gly Phe Ser Leu Ser Asn Asn Ser Leu Leu Val Pro Thr Ser Gly Ile Tyr Phe
Val Tyr Ser Gln Val Val Phe Ser Gly Lys Ala Tyr Ser Pro Lys Ala Thr Ser
Ser Pro Leu Tyr Leu Ala His Glu Val Gln Leu Phe Ser Ser Gln Tyr Pro Phe
His Val Pro Leu Leu Ser Ser Gln Lys Met Val Tyr Pro Gly Leu Gln Glu Pro
Trp Leu His Ser Met Tyr His Gly Ala Ala Phe Gln Leu Thr Gln Gly Asp Gln
Leu Ser Thr His Thr Asp Gly Ile Pro His Leu Val Leu Ser Pro Ser Thr Val
   +171
Phe Phe Gly Ala Phe Ala Leu
```

FIG. 2

```
Sau3A
GATCCCCGGC CTGCCTGGGC CTGGGCCTTG GTTCTCCCCA TGACACCACC TGAACGTCTC TTCCTCCCAA

GGGTGTGTGG CACCACCCTA CACCTCCTCC TTCTGGGGCT GCTGCTGGTT CTGCTGCCTG GGGCCAGGG

GCTCCCTGGT GTTGGCCTCA CACCTTCAGC TGCCCAGACT GCCCGTCAGC ACCCCAAGAT GCATCTTGCC
     BbvI
CACAGAGACCC TCAAACCGTC TGCTCACCTC ATTGGAGACC CCAGCAAGCA GAACTCACTG CTCTGGAGAG

CAAACACGGA CCGTGCCTTC CTCCAGGATG GTTTCTCCTT GAGCAACAAT TCTCTCCTGG TCCCCACCAG
          AccI
TGGCATCTAC TTCGTCTACT CCCAGGTGGT GGTCCAGGTC CTTCTCTGGG AAAGCCTACT CTCCCAAGGC CACCTCCTCC

CCACTCTACC TGGCCCATGA GGTGTATCCA GGGCTGCAGG AACCCTGGCT GCACTCGATG TACCACGGGG CTGCGTTCCA

CCCAGAAGAT GGTGTATCCA GGGCTGCAGG AACCCTGGCT GCACTCGATG TACCACGGGG CTGCGTTCCA

GCTCACCCAG GGAGACCAGC TATCCACCCA CACAGATGGC ATCCCCCACC TAGTCCTCAG CCCTAGTACT

GTCTTCTTTG GAGCCTTCGC TCTGTAGAAC TTTCAGGGGT CGTCACCACC TCTCCTTTGG CCATTCCAAC

CTTCTCCCCA TTCTGCCTCC ATTCTGACCA TTTCAGGGGT CGTCACCACC TCTCCTTTGG CCATTCCAAC
Sau3A
AGCTCAAGTC TTCCCTGATC
```

*FIG. 3*

N-TERMINAL DELETIONS OF LYMPHOTOXIN, THEIR PREPARATION AND USE

BACKGROUND OF THE INVENTION

1. Field of the Invention

The invention relates to new polypeptides having lymphotoxin activity or lymphotoxin-like activity, to their preparation and to their use for controlling diseases, where appropriate in combination with lymphokines.

2. Description of Related Art

Lymphotoxin (also called TNF-beta) was described for the first time in 1968 (Ruddle and Waksman J. exp. Med. 128 (1968) 1267-1279; Granger and Kolb J. Immun. 101 (1968) 111-120; Rosenau, W. Fed. Proc. 27 (1968) 34-38). As a biological factor from mitogen-stimulated lymphocytes, lymphotoxin has cytotoxic activity on neoplastic cell lines. It has a spectrum of activities, such as cytostasis of some tumor cell lines and a pronounced cytolytic activity on other transformed cells (Sawada and Osawa Jap. J. Exp. Med. 46 (1976) 263-267; Granger et al. J. Cell. Immun. 38 (1978) 388-402; Rundell and Evans Immunopharmacology 3 (1981) 9-18; Granger et al. J. Lymphokine Res. 1 (1982) 45-49; Ruddle et al. J. Lymphokine Res. 2 (1983) 23-31).

The cytotoxic activity of lymphotoxin on primary cell cultures and normal cell lines is less or nonexistent. These findings led to in vivo studies (Khan et al. Proc. Soc. exp. Biol. Med. 169 (1982) 291-294; Papermaster et al. Cancer 45 (1980) 1248-1253; Ransom et al J. Natn. Cancer Inst. 69 (1982) 741-744) whose results then showed that lymphotoxin is an effective antitumor agent.

Human lymphotoxin has the amino acid sequence depicted in FIG. 1 (Gray et al. Nature 312 (1984) 721-724). The signal sequence of lymphotoxin is labeled −34 to −1 in this figure.

Human lymphotoxin (TNF-beta) belongs to a group of lymphokines which also includes tumor necrosis factor (TNF or TNF-alpha). The two proteins not only have a similar spectrum of actions in vitro and in vivo but also act in each case synergistically with interferon-gamma (Ruddle et al. J. Lymphokine Res. 2 (1983) 23-31, Granger et al. J. Lymphokine Res. 1 (1982) 45-49; Ruff and Giffort, Lymphokines Vol. 2, Pick, E. ed. 235-275 Academic Press New York 1981; Carswell et al. Proc. Natl. Acad. Sci. 72 (1975) 3666-3670; Evans Canc. Immunol. Immunother 12 (1982) 181-190; Rundell and Evans, Immunopharmacology 3 (1981) 9-18; Ruff and Giffort, Infect. Immun. 31 (1981) 380-385; Williamson et al. Proc. Natl. Acad. Sci. 80 (1983) 5397-5401; Williams and Bellanti, J. Immunol. 130 (1983) 518-520; Stone-Wolff et al. J. Exp. Med. 159 (1984) 828-843; Lee et al. J. Immunol. 133 (1984) 1083-1086; Powell et al. J. Lymphokine Res. 4 (1985) 13-26).

The genes for the two proteins are located adjacently on chromosome 6 (Nedwin et al. Nucl. Acid Res. 13 (1985) 6361-6373).

Comparison of the amino acids of the two proteins showed that they have a 30% homology at the amino acid level (FIG. 2). This homology is concentrated on the central and C-terminal parts of the two proteins, whereas the N-terminal ends are heterologous and of different lengths (FIG. 2).

In addition, a lymphotoxin mutant is known and is distinguished from the natural lymphotoxin by the absence of the first 23 amino acids at the N-terminal end.

SUMMARY OF THE INVENTION

We have found that polypeptides which are composed of the amino acid sequences 25-171 and 26-171 of lymphotoxin and may contain in addition, at the N-terminal end, a methionyl or alanyl radical and/or a peptide sequence having immunogenic activity have more advantageous properties.

Peptide sequences having immunogenic activity may be part-sequences of known lymphokines such as, for example, TNF or interferon-gamma, or peptide sequences having special properties such as, for example, affinity for fibrin.

The new peptides can be prepared by
a) isolation of the mRNA from a lymphotoxin-producing cell line,
b) making a corresponding double-stranded cDNA copy of this mRNA,
c) insertion of this cDNA into vectors of *E. coli*,
d) transformation of *E. coli* with the resulting new vectors,
e) selection and characterization of the lymphotoxin cDNA clones using gene probes and hybridization,
f) multiplication and isolation of the vectors containing the lymphotoxin gene,
g) isolation of the gene or gene fragments using restriction endonucleases,
h) insertion of the gene or gene fragments with suitable oligonucleotides into expression vectors,
i) where appropriate, insertion of additional DNA sequences at the 5' end of the genes,
j) transformation of *E. coli* with these expression vectors, and
k) expression, isolation and purification of the desired gene product.

To isolate the corresponding cDNA, the lymphoblastoid cell line RPMI 1788 (ATCC No. CCL 156) was cultivated as described (Aggarwal et al. J. Biol. Chem. 259 (1984) 686-691) and, after stimulation, the mRNA was isolated and converted into cDNA by a conventional method.

This cDNA clone has the sequence depicted in FIG. 3. Parts of this sequence which can readily be obtained by enzymatic cleavage at restriction recognition sites are used to clone the new lymphotoxin-like polypeptides which are described in detail in the examples. The gene fragments were incorporated in cloning vectors, for example in the commercially available plasmids pUC18 and pUC19, by published methods (Maniatis et al., Molecular Cloning, Cold Spring Harbor Laboratory 1982). It is also possible to provide the genes or gene fragments with suitable chemically synthesized control regions which make expression of the proteins possible. The transformation of the resulting hybrid plasmids into suitable host organisms, preferably *E. coli*, is likewise known and described in detail. It is also possible to provide the hybrid plasmids with appropriate signal sequences which permit secretion of the polypeptides into the *E. coli* periplasm. The proteins obtained in this way have no methionine at their N-terminal end after secretion but usually do have an amino acid which is important for the cleavage site, such as, for example, alanine (Nucl. Acid Res. 8 (1980) 3011-3027).

However, because of the degeneracy of the genetic code it is also possible to use other DNA sequences, for example chemically synthesized genes with a different DNA sequence, for expression of the new polypeptides.

The new peptides can be used for oncoses, for immune diseases or for inflammatory diseases such as rheumatism or polyarthritis.

The action of the new peptides can be enhanced in a superadditive manner by the addition of lymphokines such as, for example, TNF-α and, in particular, interferon-gamma. Thus the invention also relates to combinations of the new peptides with lymphokines such as TNF-α and, in particular, interferon-gamma.

Hence the invention also relates to pharmaceuticals which contain one or more of the new polypeptides, where appropriate in a pharmaceutically tolerated vehicle or excipient. In addition the invention relates to pharmaceuticals containing combinations of the new proteins with known lymphokines or lymphokine mutants (for example interferon-gamma; TNF).

Further embodiments of the invention are described in detail in the examples which follow. The lymphotoxin used as comparison substance was cloned and expressed in E. coli in a manner analogous to that for the lymphotoxin mutants, and was purified as described.

BRIEF DESCRIPTION OF THE DRAWINGS

FIG. 1 presents the amino acid sequence of Lymphotoxin with signal sequence.

Figure 2:
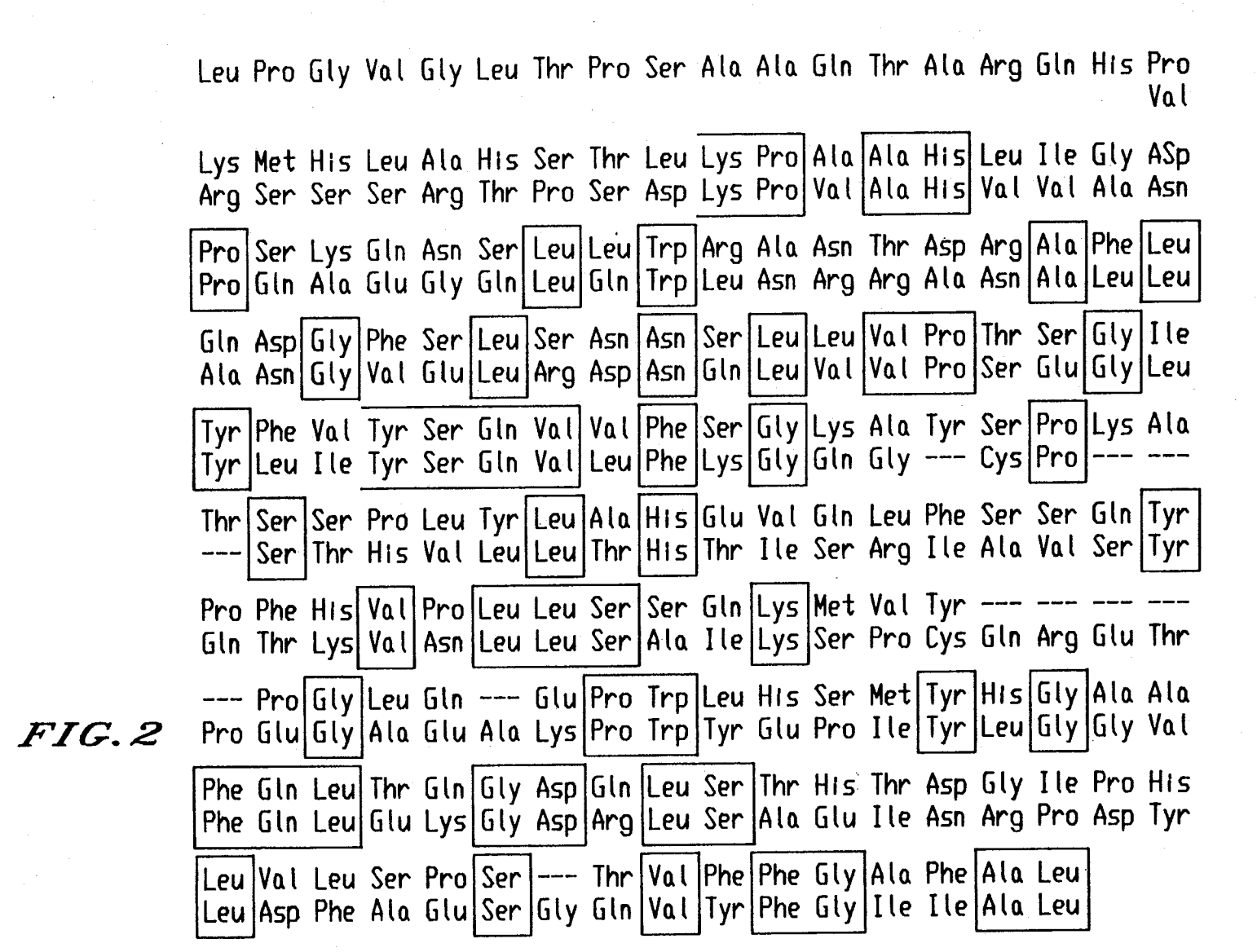

FIG. 2 presents a comparison of the amino sequences of human Lymphotoxin and human tumor necrosis factor without signal sequences.

FIG. 3 presents the cDNA sequence of a human Lymphotoxin clone.

DETAILED DESCRIPTION

1. Preparation of the cDNA

Figure 4:
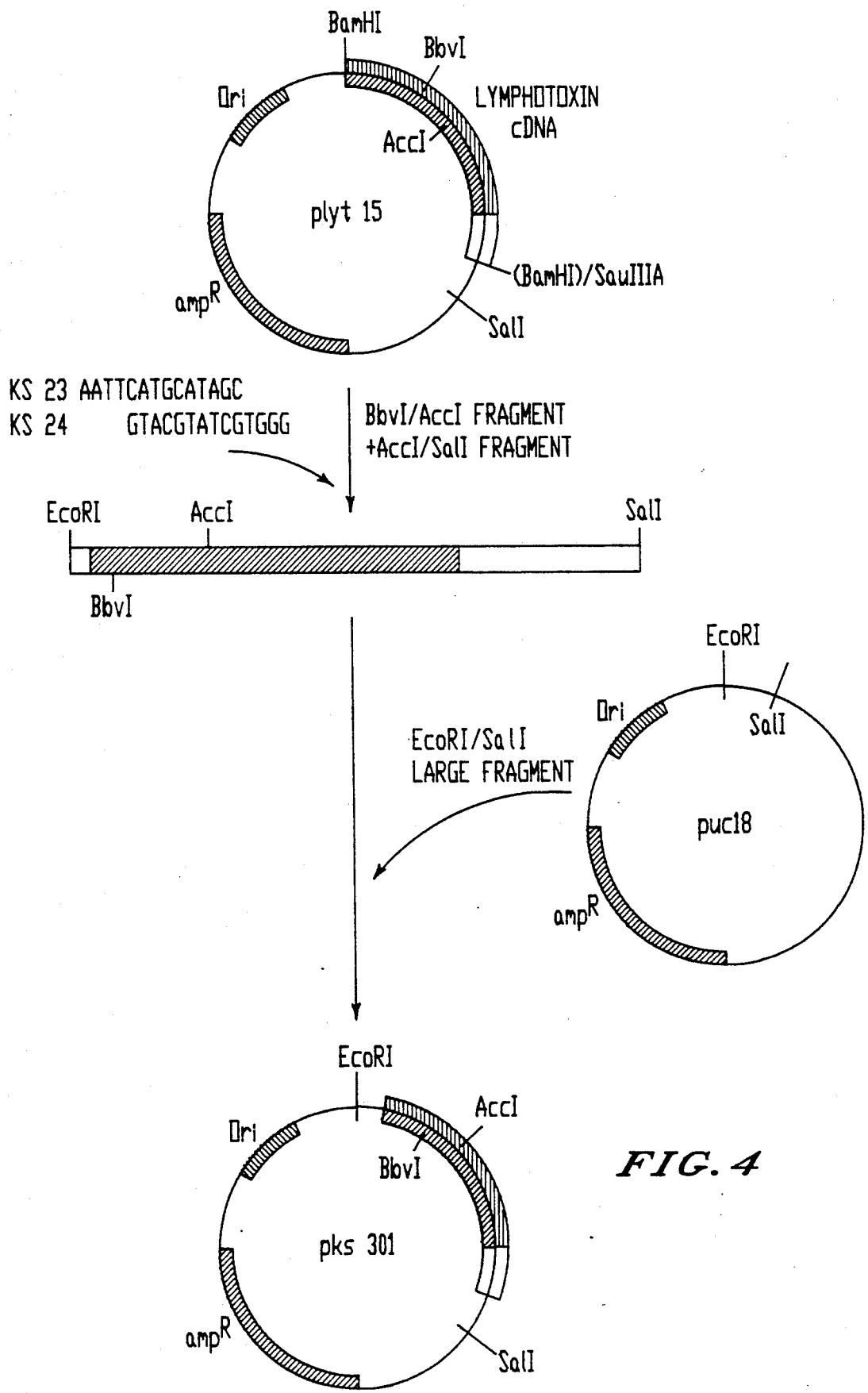
FIG. 4 displays the procedure for preparing a hybrid plasmid which contains the gene fragment for the comparison substance with the amino acid sequence 24–171.
Figure 5:
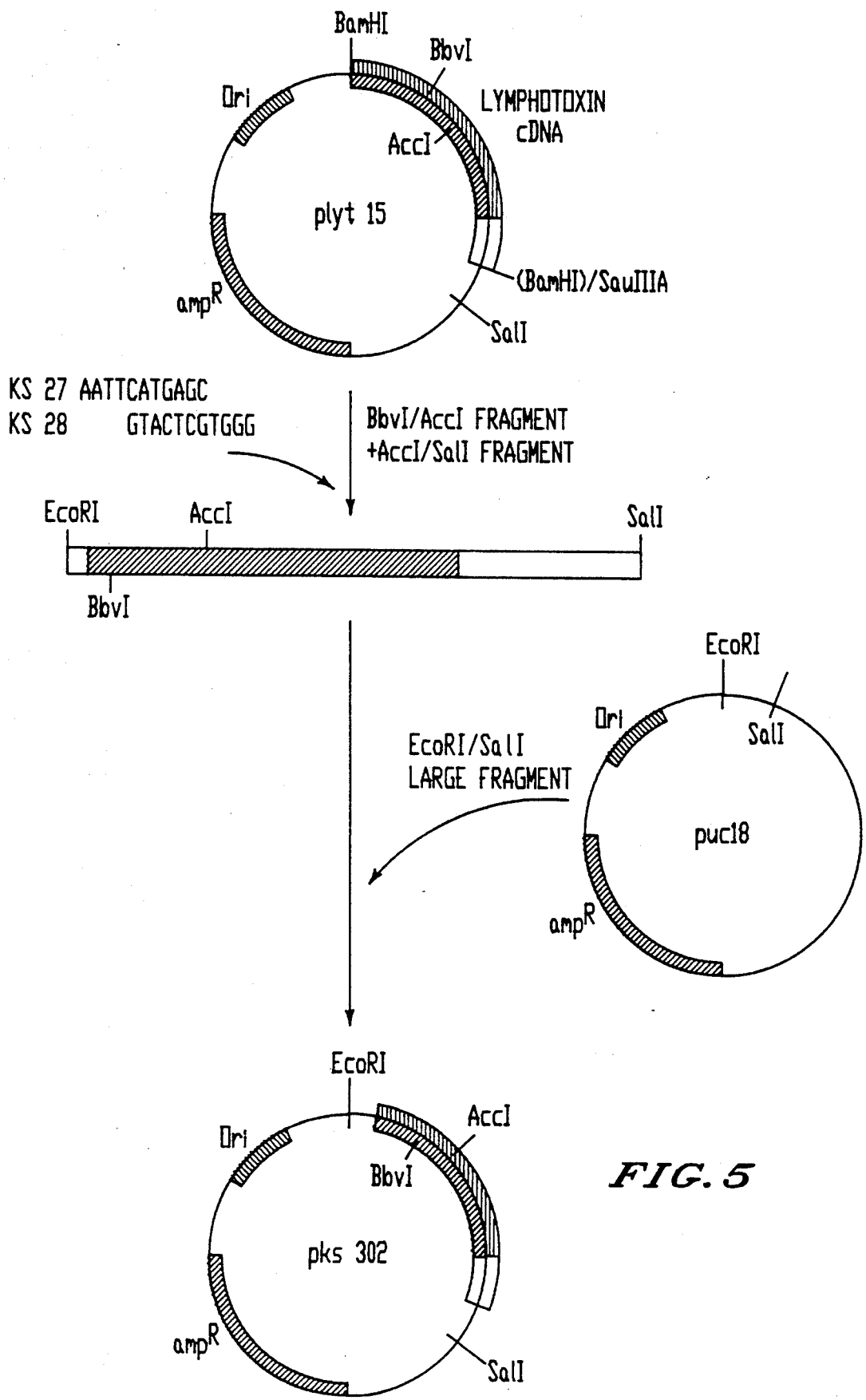
FIG. 5 displays the procedure for obtaining the hybrid plasmid which contains the gene fragment for the polypeptide with the amino acid sequence 25–171.
Figure 6:
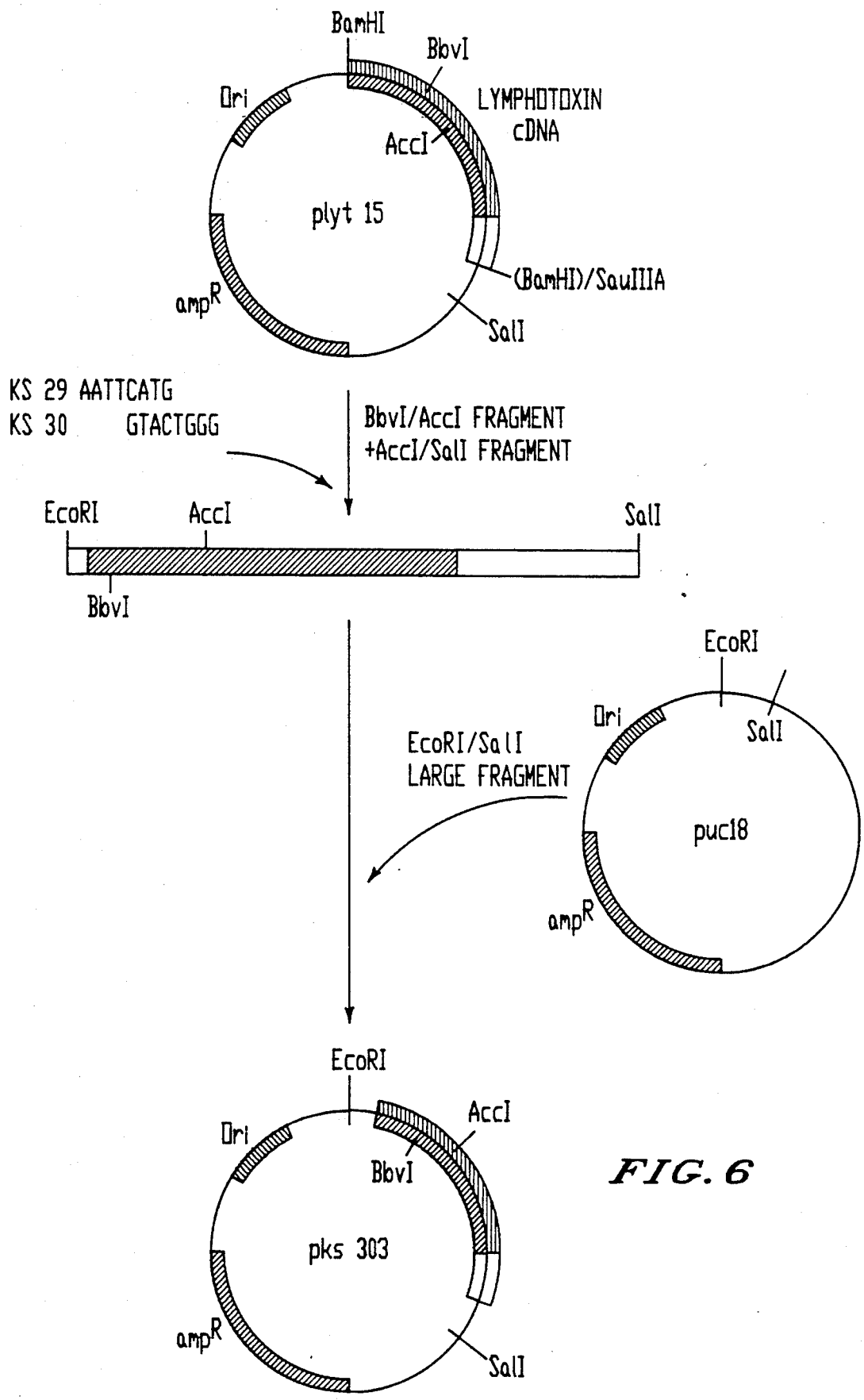
FIG. 6 displays the procedure for obtaining the hybrid plasmid which contains the gene fragments for the polypeptide with the amino acid sequence 26–171.

Culturing of the lymphotoxin(TNF-β)-producing cell line RPMI 1788

The hemopoietic cell line RPMI 1788 obtained from ATCC (No. CCL 156) was cultivated in RPMI 1640 medium containing 20% fetal calf serum in spinner bottles at 37° C. and 5% $CO_2$. After a cell density of $7-8 \times 10^5$ cells/ml had been reached, the medium was replaced by RPMI 1640 medium containing 5% fetal calf serum, and the tumor promoter PMA (4β-phorbol 12β-myristate 13α-acetate) was added in the concentration of 150 nM which had previously been found to be optimal. Maximum amounts of lymphotoxin (700 U/ml) had been produced after 70 h. The biological activity was determined as described (Aggarwal, B. B., Moffat, B. and Harkins, R. N. J. Biol. Chem. 259 (1984) 686–691). After this time, the cells were collected, washed with 2 ml of PBS and disrupted in a lysis buffer (6 M guanidinium thiocyanate, 5 mM sodium citrate, pH 7.0, 0.1 M 2-mercaptoethanol, 0.5% sarcosyl) using a homogenizer. The RNA was sedimented through a 5.7 M CsCl cushion at 35,000 rpm overnight. The poly A+-containing fraction of the mRNA was isolated and purified by affinity chromatography twice on oligo(dT)-cellulose.

The enzyme AMV reverse transcriptase was used to transliterate the poly A+ RNA into single-stranded cDNA. The second strand was likewise synthesized using reverse transcriptase. The double-stranded cDNA was cut with the restriction endonuclease Sau 3A as instructed by the manufacturer, and was fractionated on a 1% agarose gel. The DNA fragments 1 kbp ±0.5 kbp in size were eluted from the gel and ligated with dephosphorylated E. coli vector pUC 18 which had been linearized with BamHI. The DNA was transformed into competent E. coli cells of the strain HB 101, which were plated out on LB plates containing 100 μg/ml ampicillin. The bacteria were transferred onto nitrocellulose filters, replicated and lyzed, and the DNA was denatured and firmly bound to the filter.

A DNA synthesizer (Applied Biosystems, type 380 A) was used to prepare three 17mer oligonucleotide probes having homology with the published DNA sequence of human lymphotoxin. These probes had the following sequences:

5'CCTCCTGCACCTGCTGC 3'

5'TTGCTGGGGTCTCCAAT 3'

5'GAGTGCAGCCAGGGTTC 3'

The oligonucleotide probes were labeled at the 5' end with $\gamma$-$^{32}$P-ATP, and the nitrocellulose filters were incubated with the probes in 1 M NaCl, 1 mM EDTA, 1% SDS, 10% dextran sulfate, shaking at 42° C. overnight. The filters were washed thoroughly in 1 M NaCl, 1 mM EDTA, 1% SDS and then exposed to a film, and clones with sequence homologies were determined. The homologous clones were isolated and singled out. The plasmid DNA was isolated and sequenced. One of the clones isolated in this way was pLyt 15, whose sequence is depicted in FIG. 3.

2. PREPARATION OF A HYBRID PLASMID WHICH CONTAINS THE GENE FRAGMENT FOR THE COMPARISON SUBSTANCE WITH THE AMINO ACID SEQUENCE 24–171 (DELTA 23 LYMPHOTOXIN)

The starting point is the plasmid pLyt 15. It is obtained by insertion of the lymphotoxin cDNA (FIG. 3) which has been cut with Sau3A into the BamHI recognition site of pUC18. The plasmid pLyt 15 was opened in a conventional manner using the restriction endonucleases BbvI/AccI and AccI/SalI as instructed by the manufacturer (FIGS. 3 and 4). The digestion mixture was fractionated by electrophoresis on a 5% polyacrylamide gel in a conventional manner, and the fragments were visualized by staining with ethidium bromide. The two lymphotoxin gene fragments which were required, BbvI/AccI and AccI/SalI, were then cut out of the acrylamide gel and removed from the matrix by electrophoresis. 0.1 pmol of the two fragments was then ligated with 0.1 pmol of vector (pUC18 EcoRI/SalI) and the synthetic oligonucleotide KS 23/24 at 15° C. overnight.

KS23: 5'AATTCATGCATAGC3'

KS24: 3'GTACGTATCGTGGG3'

The hybrid plasmid pKS301 as shown in FIG. 4 was obtained.

3. PREPARATION OF A HYBRID PLASMID WHICH CONTAINS THE GENE FRAGMENT FOR THE POLYPEPTIDE WITH THE AMINO ACID SEQUENCE 25–171 (DELTA 24 LYMPHOTOXIN)

The starting point is the plasmid pLyt 15. It is obtained by insertion of the lymphotoxin cDNA (FIG. 3) which has been cut with Sau3A into the BamHI recognition site of pUC18. The plasmid pLyt 15 was opened in a conventional manner using the restriction endonucleases BbvI/AccI and AccI/SalI as instructed by the manufacturer (FIGS. 3 and 5). The digestion mixture was fractionated by electrophoresis on a 5% polyacrylamide gel in a conventional manner, and the fragments were visualized by staining with ethidium bromide. The two lymphotoxin gene fragments which were required, BbvI/AccI and AccI/SalI, were then cut out of the acrylamide gel and removed from the matrix by electrophoresis. 0.1 pmol of these two fragments was then ligated with 0.1 pmol of vector (pUC18 EcoRI/SalI) and the synthetic oligonucleotide KS 27/28 at 15° C. overnight.

KS27: 5'AATTCATGAGC3'

KS28: 3'GTACTCGTGGG5'

The hybrid plasmid pKS302 shown in FIG. 5 was obtained.

4. PREPARATION OF A HYBRID PLASMID WHICH CONTAINS THE GENE FRAGMENT FOR THE POLYPEPTIDE WITH THE AMINO ACID SEQUENCE 26-171 (DELTA 25 LYMPHOTOXIN)

The hybrid plasmid was constructed as described in Examples 2 and 3, using the new oligonucleotides KS29/30.

KS29: 5'AATTCATG3'

KS30: 3'GTACTGGG5'

The new hybrid plasmid pKS303 (see FIG. 6) was obtained in analogy to Examples 2 and 3.

5. TRANSFORMATION OF THE HYBRID PLASMIDS

Competent *E. coli* cells, for example W3110 (ATCC 27325), were transformed with 0.1-1 μg of the hybrid plasmids pKS301, pKS302 and pKS303 and plated out on ampicillin-containing agar plates. It was then possible to identify clones which contain correctly integrated lymphotoxin part-sequences by rapid analyses of the plasmids.

6. EXPRESSION OF POLYPEPTIDES HAVING LYMPHOTOXIN ACTIVITY

The hybrid plasmids obtained in Examples 2, 3 and 4 were provided, in a conventional manner, in their unique EcorI site with synthetically prepared signal sequences for expression. These new expression plasmids were transformed into *E. Coli.* The production cells were cultivated in normal complete medium (10 g/l peptone, 5 g/l yeast extract, 10 g/l NaCl and 100 mg/l ampicillin). The following medium was used to produce the lymphotoxin and the lymphotoxin mutants:

| | |
|---|---|
| Yeast extract, Difco | 20 g/l |
| NZ Amine A, Sheffield | 20 g/l |
| $K_2HPO_4$ | 4 g/l |
| $KH_2PO_4$ | 1 g/l |
| $NH_4Cl$ | 1 g/l |
| $CaCl_2.2H_2O$ | 0.01 g/l |
| $MnCl_2.4H_2O$ | 0.2 g/l |
| $K_2SO_4$ | 2.6 g/l |
| $MgSO_4.7H_2O$ | 0.5 g/l |
| EDTA | 0.05 g/l |
| $FeCl_3.6H_2O$ | 0.005 g/l |
| ZnO | 0.0005 g/l |
| $CuCl_2.2H_2O$ | 0.0001 g/l |
| $Co(NO_3)_2.6H_2O$ | 0.0001 g/l |
| $NH_4$ molybdate.$4H_2O$ + | 0.0001 g/l |
| 100 mg/l ampicillin | |
| pH restricted to 7.0 | |

7. PURIFICATION AND CHARACTERIZATION OF LYMPHOTOXIN COMPARISON SUBSTANCE 136 g wet mass of a lymphotoxin-producing *E. coli* strain (cf. EP 164 965), which was obtained by centrifugation of appropriate lymphotoxin-expressing shake cultures, were mixed with 800 ml of 20 mM sodium phosphate buffer, 400 mM arginine-HCl, pH 8.5. The suspended cells were disrupted by ultrasound treatment at 4° C. The nucleic acids were precipitated with 20 ml of 2 M $MnCl_2$ solution, adjusting the pH to 7.2 with 12.5% ammonia solution. The precipitate was centrifuged and removed, and 390 g of ammonium sulfate were added to the stirred supernatant at 4° C. The mixture was centrifuged, and the supernatant was discarded, and then the protein precipitate was dissolved in 200 ml of 20 mM sodium phosphate buffer, 0.1 mM arginine.HCl, pH 8.5. Dialysis against this buffer was followed by successive ion exchange chromatographies on Q-Sepharose, S-Sepharose and Mono Q (supplied by Pharmacia). ELISA determination showed that the resulting lymphotoxin solution contained from 0.01 to 0.05% residual *E. coli* proteins. N-terminal sequencing showed that the product was a mixture of the following lymphotoxin derivatives:

1) Met Lymphotoxin Met-Leu-Pro-Gly-Val-Gly-Leu-Thr-Pro-Ser
2) delta 3 Lymphotoxin Val-Gly-Leu-Thr-Pro-Ser-Ala-Ala-Gln-Thr
3) delta 23 Lymphotoxin His-Ser-Thr-Leu-Lys-Pro-Ala-Ala-His-Leu

8. PURIFICATION AND CHARACTERIZATION OF THE DELTA 23 LYMPHOTOXIN COMPARISON SUBSTANCE 20 g of *E. coli* cells which had been spun down from appropriate shake cultures (see Examples 2+6) were taken up in 200 ml of 20 mM sodium phosphate buffer, pH 8.5, and the mixture was treated with ultrasound for 15 minutes and then 4 ml of 2 M $MnCl_2$ solution were added to precipitate the nucleic acids. After centrifugation, the supernatant was adjusted to pH 8.9 with dilute ammonia solution, and the crude protein was precipitated with 78 g of ammonium sulfate. The precipitate was centrifuged and isolated, dissolved in 100 ml of 10 mM sodium phosphate buffer, pH 9.0, and was dialyzed against this buffer. Chromatography on Q-Sepharose and S-Sepharose (supplied by Pharmacia) resulted in a homogeneous protein solution which contained delta 23 lymphotoxin with methionine at the N-terminal end and in a purity exceeding 99% (according to SDS gel electrophoresis analysis). The protein had the N-terminal sequence Met-His-Ser-Thr-Leu-Lys-Pro-Ala-Ala-His-Leu-Ile.

9. PURIFICATION AND CHARACTERIZATION OF THE DELTA 24 LYMPHOTOXIN 110 g of wet biomass from appropriate *E. coli* shake cultures producing delta 24 lymphotoxin (see Examples 3+6) were, after centrifugation, suspended in 1 l of buffer (20 mM sodium phosphate, 400 mM arginine.HCl, pH 8.5) and disrupted by treatment with ultrasound at 4° C. 20 ml of 2 M $MnCl_2$ solution were added to the resulting suspension to precipitate the nucleic acids. After 1.5 h, the soluble protein fraction was obtained by centrifugation. The pH of this solution was adjusted to 8.9 using dilute ammonia solution. The delta 24 lymphotoxin was precipitated by addition of 390 g of ammonium sulfate (60% saturation) at 4° C., with stirring. The ammonium sulfate precipitate was dissolved in 300 ml of buffer (20 mM sodium phosphate, 0.1 mM arginine.HCl, pH 10.5) and dialyzed against this buffer (20 l) overnight. The dialyzed protein solution was chromatographed on an anion exchanger column (Q-Sepharose-ff, supplied by Pharmacia). For final purification, the protein was subjected to successive chromatography on CM-Sepharose (supplied by Pharmacia) and S-Sepharose. SDS polyacrylamide gel electrophoresis showed that the purity of the protein was greater than 99%. The protein was free of N-terminal methionine. The N-terminal sequence is Ser-Thr-Leu-Lys-Pro-Ala-Ala-His-Leu-Ile.

10. PURIFICATION AND CHARACTERIZATION OF THE DELTA 25 LYMPHOTOXIN 176 g of wet biomass from *E. coli* shake cultures producing delta 25 lymphotoxin (see Examples 4+6) were, after centrifugation, suspended in 600 ml of buffer (20 mM sodium phosphate, 400 mM arginine, pH 8.5). The cells were disrupted by treatment with ultrasound at 4° C. The suspension was adjusted with 2 M $MnCl_2$ solution to a final content of 40 mM to precipitate the nucleic acids. At the same time, the pH was adjusted to 7.5 with 12.5% ammonia solution. After centrifugation, 390 g of ammonium sulfate per liter of supernatant were added at 4° C. to precipitate the delta 25 lymphotoxin. The precipitate was dissolved in 300 ml of 20 mM sodium phosphate buffer, pH 10.5. The cloudy solution was centrifuged to remove insoluble protein aggregates. The supernatant was dialyzed against 5 mM sodium phosphate buffer, pH 8.5, and then chromatographed on a Q-Sepharose column (supplied by Pharmacia). For final purification, the fraction containing delta 25 lymphotoxin was subjected to successive chromatography on CM-Sepharose and Q-Sepharose (both supplied by Pharmacia). SDS polyacrylamide gel electrophoresis showed that the purity of the resulting protein was greater than 99%. Depending on the fermentation conditions, the protein contains little or no N-terminal methionine, and the N-terminal sequence was determined to be Thr-Leu-Lys-Pro-Ala-Ala-His-Leu-Ile-Gly.

11. IN VITRO CYTOTOXIC ACTIVITY OF HUMAN RECOMBINANT LYMPHOTOXIN (LT) AND DELTA 23, DELTA 24 AND DELTA 25 LT MUTANTS TOWARDS THE TNF- AND LYMPHOTOXIN-SENSITIVE CELL LINES L929 AND WEHI-164

$5 \times 10^3$ freshly trypsinized cells in the exponential phase of growth were plated out in 125 µl of complete growth medium (MEM with Earle's salts +10% FCS, Flow Laboratories, Meckenheim, FRG) in 96-well plates and incubated overnight at 37° C. and 5% $CO_2$ in an atmosphere saturated with water vapor. The substance was added the next day in 25 µl of complete culture medium per well. The initial concentration was 10 ng of protein per ml in each case; 2 duplicate titrations were carried out in series. The following controls were also set up on each culture plate: a) only culture medium; b) cells with culture medium but without lymphotoxin; c) a titrated TNF standard of known biological activity. After incubation for a further 48 h under the conditions indicated above, the surviving cells were stained with a solution of crystal violet (15 g of crystal violet, 7 g of NaCl, 646 ml of ethanol, 172.8 ml of 37% formaldehyde made up to 2 l with $H_2O$. This entailed the culture medium being drained off and then the cells being stained with 50 µl of the solution at room temperature for 20 min. The culture plates were then washed with water until all the dyestuff which was not cell-bound had been removed. The cell-bound dyestuff was determined by photometry, after addition of 100 µl of measurement solution (50% ethanol, 0.1% acetic acid), at 540 nm using a Titertek Multiscan MCC/340 (Flow Laboratories, Meckenheim). The concentrations of lymphotoxin or LT mutants which result in 50% lysis of the cells compared with the untreated cell control (measured by the reduction in absorption) have been stated.

One unit (U) is defined as the amount of lymphotoxin or LT mutant which induces 50% lysis of the given number of cells.

The resultant biological activities for the indicator cell line L929 are as follows (corrected by comparison with the control TNF standard with an activity of $8.2 \times 10^6$ U/mg protein):

| Substance | Activity (U/mg protein) |
|---|---|
| Lymphotoxin (LT) | $6.1 \times 10^7$ |
| delta 23LT | $1.2 \times 10^8$ |
| delta 24LT | $2.0 \times 10^8$ |
| delta 25LT | $8.5 \times 10^7$ |

The biological activities towards the tumor cell line WEHI-164 for the lymphotoxin and LT mutants are as follows (the protein concentrations which bring about 50% lysis of a given number of cells are indicated):

| Substance | Protein concentration $EC_{50}$ (ng protein/ml) |
|---|---|
| LT | 0.55 |
| delta 23LT | 0.29 |
| delta 24LT | 0.15 |
| delta 25LT | 0.38 |

12. SYNERGISTIC CYTOTOXIC ACTIVITY OF HUMAN RECOMBINANT LYMPHOTOXIN AND ITS MUTANTS WITH RECOMBINANT INTERFERON-GAMMA ON TUMOR CELLS

To demonstrate the synergistic activity of lymphotoxin or the LT mutants with interferon-gamma, use was made of the human osteosarcoma MG-63 which is not sensitive to lymphotoxin alone but whose growth is inhibited dosedependently by interferon-gamma.

The experimental procedure was as follows:

$2 \times 10^3$ cells in the exponential phase of growth were plated out in complete culture medium (RPMI 1640+10% FCS, both from Flow Laboratories, Meckenheim) in each well of a 96-well plate and were incubated overnight at 37° C. and 5% $CO_2$ in an atmosphere saturated with water vapor. Then, maintaining the interferon-gamma (human recombinant) concentrations constant, the lymphotoxin or the lymphotoxin mutants were subjected to serial 5-fold dilution starting from a concentration of 10 ng/ml protein. The final volume was 150 μl in all the culture wells. Pure culture medium or cultivated cells without the addition of IFN-gamma and/or LT or LT mutants were used as controls. The culture plates were incubated for a further 72 h under the conditions indicated above and were then stained using the crystal violet stain as described under

11. AND EVALUATED BY PHOTOMETRY.

Figure 7:
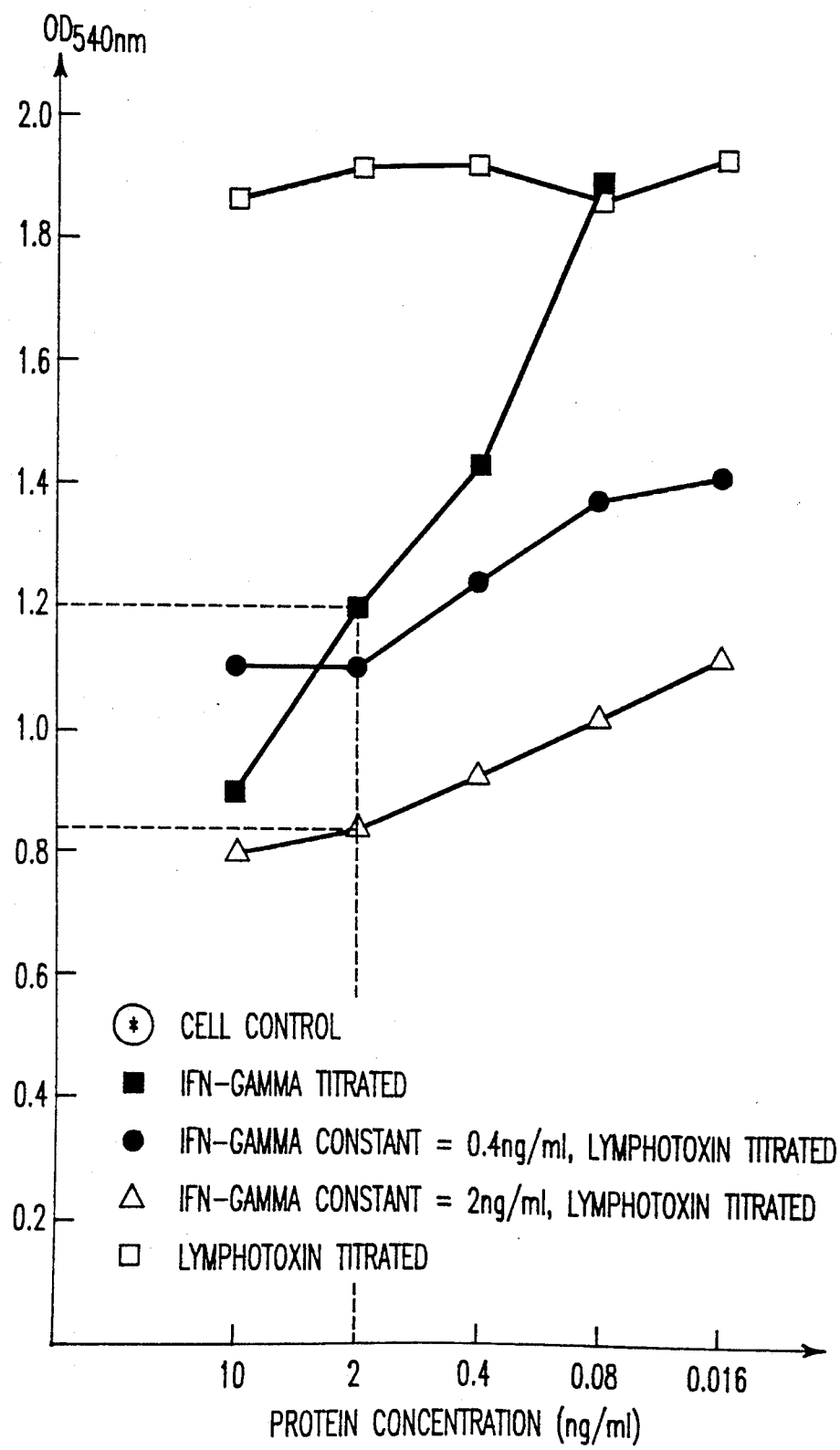
FIG. 7 displays the synergistic effect of interferon-gamma and Lymphotoxin against MG-63 tumor cells.

The experimental data on the determination of the synergistic effect of interferon-gamma and lymphotoxin against the MG-63 tumor cell line are depicted in FIG. 7.

The synergistic action of lymphotoxins with interferon-gamma was determined as follows:

a) the antiproliferative activity of interferon-gamma was determined from the optical densities of the samples by the following formula:

$$\text{IFN-gamma activity} = 100\% - \frac{\text{OD 540 nm of the treated cells}}{\text{OD 540 nm of the cell control}} \times 100\% \quad (A)$$

Example: 2 ng/ml IFN-gamma; see FIG. 7 in this context $$\text{IFN-gamma activity: } 100\% - \frac{1.20}{1.85} \times 100\% = 35\%.$$

b) Determination of the cytotoxic activity of the combination of interferon-gamma and lymphotoxin using formula A.

Example: 2 ng/ml interferon-gamma and 2 ng/ml LT; see FIG. 7 in this context $$\text{IFN-gamma + LT activity} = 100\% - \frac{0.83}{1.85} \times 100\% = 55\%.$$

c) Determination of the synergistic effect of lymphotoxins with interferon-gamma:

$$\text{Synergistic effect} = \frac{\text{IFN-}\gamma + \text{LT activity}}{\text{IFN-}\gamma \text{ activity}}$$

Example 2 ng/ml IFN-gamma and 2 ng/ml lymphotoxin; see FIG. 7 and Examples 12a +b in this context $$\text{Synergistic effect} = \frac{55\%}{35\%} = 1.57$$

The combination of 2 ng/ml of interferon-gamma with 2 ng/ml lymphotoxin enhances the cytotoxic effect induced by 2 ng/ml interferon-gamma alone by a factor of 1.57. A figure of 1.41 was obtained in a second measurement. The mean of the two figures (1.49) is shown in the Table on page 15.

Figure 8:
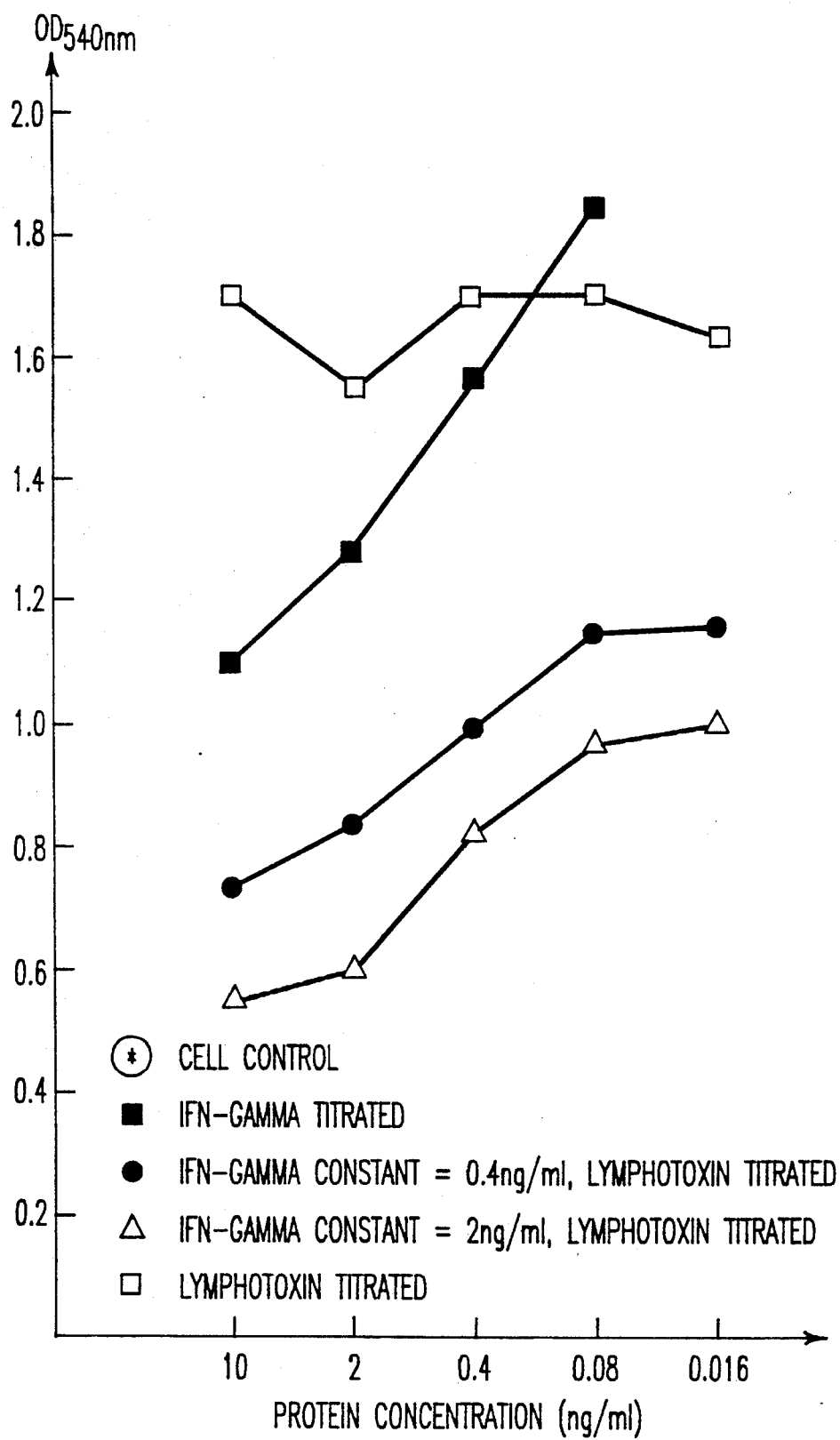
FIG. 8 displays the synergistic effect of interferon-gamma and delta 24 Lymphotoxin against MG-63 tumor cells.

The experimental data for the determination of the synergistic effect of interferon-gamma and of the lymphotoxin mutant delta 24 against the MG-63 tumor cell line are depicted in FIG. 8. The synergistic action of delta 24 LT with interferon-gamma was determined as shown hereinbefore.

The results showing the enhancement of the cytotoxicity induced by interferon-gamma (synergistic effect) by combination with lymphotoxin or one of the lymphotoxin mutants described here are compiled in the Table which follows.

| LT species | IFN-gamma (ng/ml) | Amount of Lymphotoxin (ng/ml) used | | | | |
|---|---|---|---|---|---|---|
| | | 10 | 2 | 0.4 | 0.08 | 0.016 |
| LT | 2.0 | 1.61 | 1.49 | 1.40 | 1.27 | 1.15 |
| | 0.4 | 2.16 | 1.89 | 1.75 | 1.87 | 1.42 |
| delta23 | 2.0 | 1.48 | 1.38 | 1.32 | 1.16 | 1.05 |
| | 0.4 | 2.0 | 1.90 | 1.62 | 1.27 | 1.24 |
| delta24 | 2.0 | 2.45 | 2.04 | 1.69 | 1.49 | 1.55 |
| | 0.4 | 6.59 | 3.75 | 2.69 | 1.96 | 2.37 |
| delta25 | 2.0 | 2.61 | 1.89 | 1.63 | 1.38 | 1.41 |
| | 0.4 | 8.30 | 3.45 | 3.04 | 1.45 | 1.65 |

The figures given in the Table were determined as explained above under 12a to 12c and represent the means of two independent experiments.

13. DETERMINATION OF TOXICITY

Male Balb/c mice from 4 to 6 weeks of age were used to determine the acute toxicity of the substances under investigation. The animals were randomized (5 animals in each group) and, following a one-week acclimatization period, they received various doses of the test substance (0.25–4.0 mg/kg body weight intravenously, injected into one of the lateral caudal veins). The volume administered was 10 ml/kg body weight; the injection was administered over a period of 10 seconds. The substances had been dissolved in physiological saline solution which contained 0.2% BSA (bovine serum albumin) immediately before the intravenous injection. Animals which received intravenous administration of 10 ml of physiological saline solution per kg of body weight, with 0.2% BSA, acted as controls. Following injection of the test substance, all the animals were observed for 7 days. The following signs were noted: diarrhea, diminished locomotion, piloerection, cyanosis and death; in addition, the body temperature and weight of the animals were determined at regular intervals.

The results of several investigations showed that both lymphotoxin (LT) and the mutants (delta 23LT, delta 24LT and delta 25LT) caused a dose- and time-dependent reduction in body temperature and weight and in locomotion, and induced piloerection and diarrhea. These signs were detectable as early as 2 hours after the injection, especially at higher doses, and were completely reversible in the surviving animals within the 7-day observation period. The observed signs were most pronounced in the animals which had been treated with LT. Animals which had been treated with the LT mutants showed overall less pronounced signs compared with LT, although delta 23LT caused distinctly more pronounced signs than did delta 24LT; delta 25LT occupied a position in the middle between delta 23LT and delta 24LT.

The relevant $LD_{50}$ values were estimated to be as follows:

$LD_{50}$ for LT: 0.79 mg/kg body weight
$LD_{50}$ for delta 23LT: 1.84 mg/kg body weight
$LD_{50}$ for delta 25LT: 3.1 mg/kg body weight
$LD_{50}$ for delta 24LT: could not be calculated because with no dose did 50% or more of the animals die.

We claim:

1. Polypeptides of the formula

X— Leu Lys Pro Ala Ala His Leu Ile Gly Asp Pro Ser Lys
Gln Asn Ser Leu Leu Trp Arg Ala Asn Thr Asp Arg Ala Phe
Leu Gln Asp Gly Phe Ser Leu Ser Asn Asn Ser Leu Leu Val
Pro Thr Ser Gly Ile Tyr Phe Val Tyr Ser Gln Val Val Phe
Ser Gly Lys Ala Tyr Ser Pro Lys Ala Thr Ser Ser Pro Leu
Tyr Leu Ala His Glu Val Gln Leu Phe Ser Ser Gln Tyr Pro
Phe His Val Pro Leu Leu Ser Ser Gln Lys Met Val Tyr Pro
Gly Leu Gln Glu Pro Trp Leu His Ser Met Tyr His Gly Ala
Ala Phe Gln Leu Thr Gln Gly Asp Gln Leu Ser Thr His Thr
Asp Gly Ile Pro His Leu Val Leu Ser Pro Ser Thr Val Phe
Phe Gly Ala Phe Ala Leu wherein X is Thr, Ser-Thr, Met-Thr, Met-Ser-Thr, Ala-Thr or Ala-Ser-Thr.

2. Polypeptides as claimed in claim 1, wherein X is Ser-Thr or Thr.

3. A therapeutic composition comprising a pharmaceutically acceptable carrier and an effective amount of a polypeptide as claimed in claim 1 as the active ingredient.

* * * * *